(12) United States Patent
Powell

(10) Patent No.: US 11,717,507 B2
(45) Date of Patent: *Aug. 8, 2023

(54) COMPOSITIONS AND METHODS FOR PREVENTING AND RECOVERY FROM DETRIMENTAL EFFECTS OF ALCOHOL CONSUMPTION

(71) Applicant: Cheers Health, Inc., Houston, TX (US)

(72) Inventor: Brooks Alexander Reid Powell, Houston, TX (US)

(73) Assignee: CHEERS HEALTH, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,545

(22) Filed: Nov. 3, 2022

(65) Prior Publication Data

US 2023/0089539 A1    Mar. 23, 2023

Related U.S. Application Data

(63) Continuation of application No. 16/918,391, filed on Jul. 1, 2020, now Pat. No. 11,504,353, which is a continuation of application No. 16/580,402, filed on Sep. 24, 2019, now Pat. No. 10,736,870, which is a continuation of application No. 16/514,812, filed on Jul. 17, 2019, now Pat. No. 10,478,416, which is a continuation of application No. 15/965,565, filed on Apr. 27, 2018, now Pat. No. 10,398,675, which is a continuation of application No. 15/465,081, filed on Mar. 21, 2017, now Pat. No. 9,962,365, which is a continuation of application No. 14/726,230, filed on May 29, 2015, now Pat. No. 9,603,830.

(60) Provisional application No. 62/004,479, filed on May 29, 2014.

(51) Int. Cl.
| | | |
|---|---|---|
| *A61K 31/353* | (2006.01) | |
| *A61K 31/198* | (2006.01) | |
| *A61K 36/33* | (2006.01) | |
| *A61K 31/357* | (2006.01) | |
| *A61K 36/9068* | (2006.01) | |
| *A61K 9/00* | (2006.01) | |
| *A61K 9/20* | (2006.01) | |
| *A61K 9/48* | (2006.01) | |

(52) U.S. Cl.
CPC .......... *A61K 31/353* (2013.01); *A61K 9/0095* (2013.01); *A61K 9/2009* (2013.01); *A61K 9/2013* (2013.01); *A61K 9/4858* (2013.01); *A61K 9/4875* (2013.01); *A61K 31/198* (2013.01); *A61K 31/357* (2013.01); *A61K 36/33* (2013.01); *A61K 36/9068* (2013.01)

(58) Field of Classification Search
None
See application file for complete search history.

(56) References Cited

U.S. PATENT DOCUMENTS

| | | |
|---|---|---|
| 5,759,539 A | 6/1998 | Whitmire |
| 6,485,758 B2 | 11/2002 | Mirza et al. |
| 6,827,932 B2 | 12/2004 | Crippen et al. |
| 9,474,802 B2 | 10/2016 | Burg |
| 9,603,830 B2 | 3/2017 | Powell |
| 9,744,202 B2 | 8/2017 | Burg |
| 9,962,365 B2 | 5/2018 | Powell |
| 2015/0305249 A1 | 10/2015 | Miller et al. |
| 2015/0342923 A1 | 12/2015 | Powell |
| 2017/0246143 A1 | 8/2017 | Powell |
| 2019/0029995 A1 | 1/2019 | Powell |

FOREIGN PATENT DOCUMENTS

WO    2012058589 A1    5/2012

OTHER PUBLICATIONS

"AfterPartyPalTM", http://afterpartypal.com, downloaded Sep. 29, 2015, Sep. 29, 2015, 7 pages.
"Berocca", http://buyberocca.com/en/home/, downloaded Oct. 6, 2015, Oct. 6, 2015, 3 pages.
"Blowfish for Hangovers", http://forhangovers.com/, downloaded Oct. 6, 2015, Oct. 6, 2015, 3 pages.
"BluCetin Liver and Immune Support", http://www.blucetin.com, downloaded Oct. 1, 2015, Oct. 1, 2015, 4 pages.
"Bytox", https://www.bytox.com/, downloaded Oct. 6, 2015, Oct. 6, 2015, 1 page.
"Chaser", http://www.consumersearch.com/as-seen-on-tv/chaser, downloaded Oct. 6, 2015, Oct. 6, 2015, 3 pages.
"Dihydromyricetin Depot", http://dhmdepot.com, downloaded Sep. 29, 2015, Sep. 29, 2015, 9 pages.
"Dr. P's HG3 Hangover Prevention Tablet", http://www.drphg3.com, downloaded Sep. 29, 2015, Sep. 29, 2015, 5 pages.
"Drink Ease", http://www.drinkease.com/, downloaded Oct. 6, 2015, Oct. 6, 2015, 2 pages.
"Drinkin Mate Drinkin' Mate Feel Betterthe Next Day", eVitamins. com, http://www.evitamins.com/drinkin-mate-feelbetter--drinkin-mate-14871 downloaded Sep. 9, 2015, Sep. 9, 2015, 3 pages.
"Drinkwel", http://www.drinkwel.com, downloaded Oct. 1, 2015, Oct. 1, 2015, 1 page.
"Forget Hangovers", http://forgethangovers.com/, downloaded Oct. 6, 2015, Oct. 6, 2015, 2 pages.
"GTOX Detox & Recovery Shot", https://www.facebook.com/GTOXNOW, downloaded Sep. 29, 2015, Sep. 29, 2015, 8 pages.
"Hangover Destroyer", http://hdestroyer.com/, downloaded Oct. 6, 2015, Oct. 6, 2015, 6 pages.

(Continued)

*Primary Examiner* — Michael V Meller
(74) *Attorney, Agent, or Firm* — Perkins Coie LLP

(57) ABSTRACT

Disclosed are compositions, devices, and methods to prevent and recover from detrimental effects of alcohol consumption, including significant undesirable symptoms of a hangover consciously felt by the alcohol consumer, as well as those that may not be consciously experienced. The present technology comprehensively targets multiple negative effects of hangovers. In one aspect, a composition includes dihydromyricetin (DHM); and N-acetyl cysteine (NAC). The composition may further include Prickly Pear Extract, Milk Thistle, Ginger Root, Vitamins B, C, and E, electrolytes, and/or sugars.

1 Claim, 4 Drawing Sheets

(56) References Cited

OTHER PUBLICATIONS

"Hangover Guardian: Advanced Hangover Pills", http://www.amazon.com/Hangover-Guardian-Advanced-Activated-Charcoal/dp/B00BD5K0FG, downloaded Oct. 6, 2015, Oct. 6, 2015, 7 pages.
"Hangover Salvation", http://hangoversalvation.com/, downloaded Oct. 6, 2015, Oct. 6, 2015, 4 pages.
"HangoverStopper", http://www.hangoverstopper.com/?gclid=CPqO-sKNicYCFQGnaQodYnlAuA, downloaded Oct. 6, 2015,, Oct. 6, 2015, 2 pages.
"Hang-Zen", http://drinkhangzen.com, downloaded Oct. 1, 2015, Oct. 1, 2015, 2 pages.
"Happy Hour Vitamins", http://happyhourvitamins.com/, downloaded Oct. 6, 2015, Oct. 6, 2015, 12 pages.
"KÜRE Hangover Prevention and Recovery", http://www.amazon.com/KÜRE-Prevention-Recovery-Satisfaction-Guarantee/dp/B00H4FZQ5I, downloaded Oct. 6, 2015, Oct. 6, 2015, 7 pages.
"Life Support", https://lifesupport.com, downloaded Oct. 1, 2015, Oct. 1, 2015, 5 pages.
"LifeExtension® Anti-Alcohol Antioxidants with Hepato Protection Complex", http://www.lifeextension.com/vitaminssupplements/Item01440/Anti-Alcohol-Antioxidants-with-HepatoProtection-Complex, downloaded Oct. 6, 2015, Oct. 6, 2015, 9 pages.
"Mercy Nutraceuticals, Inc.", http://webstore.drinkmercy.com, downloaded Oct. 1, 2015, Oct. 1, 2015, 1 page.
"Never Too Hungover", http://nevertoohungover.com/, downloaded Oct. 1, 2015, Oct. 1, 2015, 8 pages.
"No-Hang", http://www.nightlifesupplements.com/we-found-a-better-mousetrap-no-hang/, downloaded Oct. 6, 2015, Oct. 6, 2015, 3 pages.
"NOHO Drink", http://www.nohodrink.com/, downloaded Oct. 6, 2015, Oct. 6, 2015, 2 pages.
"PartySmart®", http://www.partysmart.net/in/flash/stage.html, downloaded Oct. 6, 2015, Oct. 6, 2015, 1 page.
"Prelgame", http://getpregame.com, downloaded Oct. 1, 2015, Oct. 1, 2015, 7 pages.
"PreToxx for Hangovers & Lover Support", http://www.amazon.com/Hangovers-Vegetarian-Capsules-Electrolyte-Guarantee/dp/B001EM7T34, downloaded Sep. 29, 2015, Sep. 29, 2015, 7 pages.
"Previtalise", https://www.facebook.com/previtalise, downloaded Oct. 6, 2015, Oct. 6, 2015, 4 pages.
"Rally Capsules", http://www.rallycapsules.com/, downloaded Oct. 6, 2015, Oct. 6, 2015, 10 pages.
"RU21 Hangover Pill", http://www.ru21.com/, downloaded Oct. 1, 2015, Oct. 1, 2015, 5 pages.
"Sobur Hangover Pills", http://www.sobur.co/, downloaded Oct. 6, 2015, Oct. 6, 2015, 8 pages.
"Source Naturals Hangover Formula™", http://www.sourcenaturals.com/products/GP1149, downloaded Oct. 1, 2015, Oct. 1, 2015, 1 page.
"Texas Hangover Cure", http://www.texashangovercure.com/, downloaded Oct. 6, 2015, Oct. 6, 2015, 1 page.
"The Hangover Recovery Shot", http://www.hangoverjoes.com/index.php, downloaded Oct. 1, 2015, Oct. 1, 2015, 4 pages.
"Toniiq", http://www.toniiq.com/, downloaded Oct. 6, 2015, Oct. 6, 2015, 5 pages.
"Trendmonitor", http://trndmonitor.com/product-spotlight-lastcall-productivity-beverage/, downloaded Oct. 1, 2015, Oct. 1, 2015, 2 pages.
"Zaca®", http://www.zacalife.com, downloaded Oct. 1, 2015, Oct. 1, 2015, 3 pages.
Braun, S , "Buzz", The Science and Lore of Alcohol and Caffeine, 1997, pp. 82-86.
Howland, Jonathan , et al., "Hangover Predicts Residual Alcohol Effects on Psychomotor Vigilance the Morning After", Journal of Addiction Research Therapy, 2010; 1(101), 11 pages.
Rohsenow, Damaris J, et al., "The Acute Hangover Scale: A new measure of immediate hangover symptoms", Addictive Behaviors, 2007, 32(6):1314-20, Jun. 2007.
Shen, Yi, et al., "Dihydromyricetin as a novel anti-alcohol intoxication medication", J. Neurosci, 2012, 32(1):390-401.
Wechsler, Henry Ph.D., et al., "Health and behavioral consequences of binge drinking in college. A national survey of students", JAMA, 1994, 272: 1672-77, 1994, 1672-77.
Wiese, Jefffrey G, et al., "The alcohol hangover", Annals of Internal Medicine, 2000; 132(11), Jun. 6, 2000, 897-902.
Atkuri, Kondala R., et al., "N-acetylcysteine—a safe antidote for cysteine/glutathione deficiency," Curr Opin Pharmacol. 7(4): 355-359, 2007.
Gould, Rebecca L., et al., "Impact of Supplementary Amino Acids, Micronutrients, and Overall Diet on Glutathione Homeostasis," Nutrients, 11, 1056, p. 1-21, 2019.
Millea, Paul J., et al., "N-Acetylcysteine: Multiple Clinical Applications," American Family Physician vol. 80, No. 3, p. 265-269, 2009.
Pedre, Brandan, et al., "The mechanism of action of N-acetylcysteine (NAC): The emerging role of H2S and sulfane sulfur species," Pharmacology & Therapeutics 228, 107916, 2021.
Plaza, Noelia Clemente, et al., "Effects of the Usage of L-Cysteine (L-Cys) on Human Health," Molecules, 23, 575, p. 1-13, 2018.
Sansone, Randy, A., et al., "Getting a knack for NAC: N-Acetyl-Cysteine," Innov Clin Neurosci. 8(1): p. 10-14, 2011.
Schmitt, Bernard, et al., "Effects of N-acetylcysteine, oral gluthathione (GSH) and a novel sublingual form of GSH on oxidative stress markers: A comparative crossover study," Redox Biology 6, p. 198-205, 2015.

COMPOSITIONS AND METHODS FOR PREVENTING AND RECOVERY FROM DETRIMENTAL EFFECTS OF ALCOHOL CONSUMPTION

CROSS-REFERENCE TO RELATED APPLICATIONS

This patent document is a continuation of U.S. patent application Ser. No. 16/918,391 filed Jul. 1, 2020, which is a continuation of U.S. patent application Ser. No, 16/580, 402, filed Sep. 24, 2019, which is a continuation of U.S. patent application Ser. No, 16/514,812, filed Jul. 17, 2019, now U.S. Pat. No. 10,478,416, issued Nov. 19, 2019, which is a continuation of U.S. patent application Ser. No, 15/965, 565, filed Apr. 27, 2018, now U.S. Pat. No. 10,398,675, issued Sep. 3, 2019, which is a continuation of U.S. patent application Ser. No. 15/465,081, filed on Mar. 21, 2017, now U.S. Pat. No. 9,962,365, issued on May 8, 2018, which is a continuation of U.S. patent application Ser. No, 14/726,230, filed on May 29, 2015, now U.S. Pat. No. 9,603,830, issued on Mar. 28, 2017, which claims the benefits and priority of U.S. Provisional Patent Application No. 62/004,479, filed on May 29, 2014. The entire contents of the before-mentioned patent applications are incorporated by reference as part of the disclosure of this application.

TECHNICAL FIELD

This patent document relates to compositions, devices, and methods for preventing and/or relieving side effects of alcohol consumption.

BACKGROUND

Alcohol is a constituent of medicines, foods, and beverages that provides both beneficial and detrimental effects on human beings. Alcohol typically refers to ethyl alcohol (ethanol), which is the common form of consumable alcohol found in alcoholic beverages, e.g., such as beer, wine, and liquor. Consumable alcohol is produced by fermentation processes of various food products, e.g., including wheat, rice, or other starches, fruits, honey, or other sources of sugars, and yeast. The National Institute of Alcohol Abuse and Alcoholism (NIAAA) of the U.S. National Institutes of Health (NIH) considers a standard drink to be equal to 0.6 ounces of pure ethanol, e.g., which is equivalent to approximately 12 fluid ounces (fl. oz.) of regular beer (of about 5% alcohol), 8-9 fl. oz. of malt liquor (of about 7% alcohol), 5 fl. oz. of wine (of about 12% alcohol), and 1.5 fl. oz. (referred to as a "shot") of an 80-proof distilled spirit or liquor (e.g., gin, rum, vodka, whiskey, tequila, etc.).

During consumption, alcohol is rapidly absorbed from the stomach and small intestine into the bloodstream, from which it can affect several organs including the brain, heart, pancreas, and liver. Alcohol can act as a depressant to the central nervous system (CNS). For example, alcohol interferes with the brain's communication pathways, which affects brain functionality that manifests in cognitive and behavioral changes, e.g., such as a person's ability to think, focus, move, as well as his/her mood and behavior. Alcohol can cause inflammation and damage to the liver, e.g., where consistent heavy drinking can cause chronic liver problems. For example, heavy drinking can lead to steatosis (e.g., or fatty liver), infection (e.g., alcoholic hepatitis), fibrosis, and cirrhosis.

SUMMARY

Disclosed are compositions, devices, and methods to prevent and recover from detrimental effects of alcohol consumption.

In one aspect, a composition includes dihydromyricetin (DHM); and N-acetyl cysteine (NAC). Implementations of the composition can include one or more of the following features. In some implementations, for example, the composition can further include prickly pear extract and/or silymarin. In some implementations, for example, the composition can further include ginger root extract, vitamin C, vitamin E, electrolytes, or one, a blend or a complex of B vitamins (e.g., thiamine, riboflavin, niacin, pantothenic acid, pyridoxine, pyridoxal, biotin, folic acid, and cobalamin). In some implementations, for example, the composition can further include carbohydrates, e.g. including a sugar.

In one aspect, a composition for mitigating adverse effects of alcohol consumption includes dihydromyricetin (DHM) to reduce hangover symptoms including one or more of sleep disruption, headache, or alcohol withdrawal effects associated alcohol consumption; and N-acetyl cysteine (NAC) to affect acetaldehyde and congeners produced by the liver associated with the alcohol consumption. Implementations of the composition can include one or more of the following features. In some implementations, for example, the composition can further include prickly pear extract provided to affect oxidative stress associated with the alcohol consumption; silymarin provided to affect liver functionality in breaking down toxic substances and to affect oxidative stress associated the alcohol consumption; and/or one or more B vitamins selected from a group consisting of thiamine, riboflavin, niacin, pantothenic acid, pyridoxine, pyridoxal, biotin, folic acid, and cobalamin, in which the one or more B vitamins are provided to replenish vitamins lost and to reduce headaches associated the alcohol consumption.

In one aspect, a method for mitigating adverse effects of alcohol consumption includes providing a dose of a first-stage composition to be consumed at a first time proximate to the beginning of alcohol consumption by a person, in which the first-stage composition includes N-acetyl cysteine (NAC) and one or both of prickly pear extract and silymarin; and providing a dose of a second-stage composition to be consumed ata second time proximate to the end of the alcohol consumption by the person, or providing a dose of the second-stage composition or a third-stage composition to be consumed at a third time after the alcohol consumption by the user, in which the second-stage composition and the third-stage composition include dihydromyricetin (DHM), NAC, and one or both of one or both of prickly pear extract and silymarin.

The subject matter described in this patent document can be implemented in specific ways that provide one or more of the following features. For example, the disclosed compositions include formulations of ingredients capable of effectively and comprehensively treating multiple symptoms of hangovers and the negative effects of alcohol. In some implementations, for example, compositions of the present technology can be used to aid in sobering up a person if taken during drinking, or keeping them sober if taken before drinking. In some implementations, for example, compositions of the present technology can be used as a daily supplement to aid in the replenishing of electrolytes of the individual, and/or reverse negative effects on brain function (e.g., through the use of DHM).

DETAILED DESCRIPTION

Figure 1:
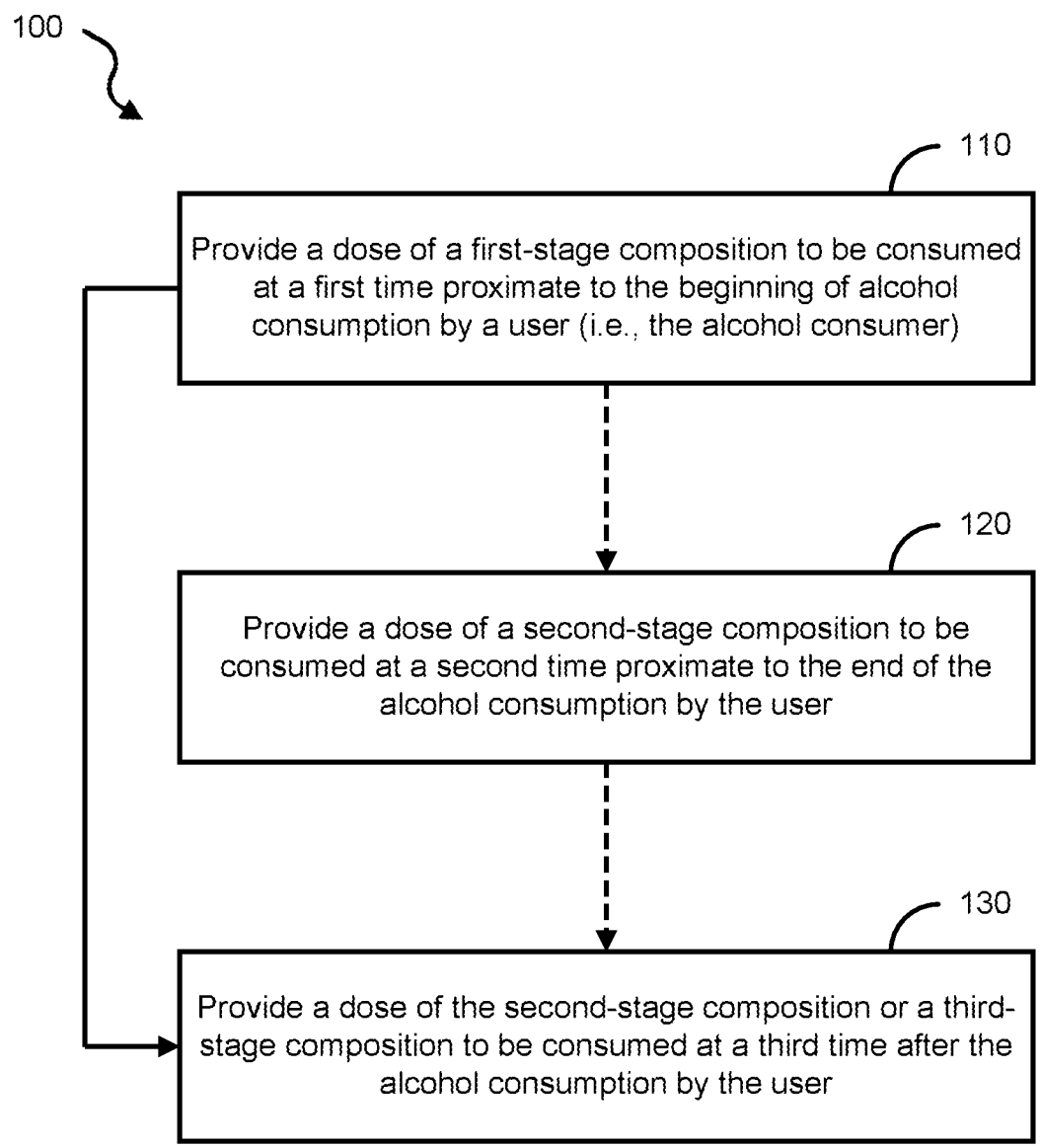
FIG. 1 shows a diagram of an exemplary method for mitigating adverse effects of alcohol consumption using a multi-staged composition of the disclosed technology.

The ingestion of alcohol has numerous effects on the human brain and body. The immediate effect of alcohol on humans is that of intoxication. This varies in degrees based on the tolerance of the individual and the amount of drinks consumed, as well as with the amount of different types of food and liquids consumed prior to drinking.

The alcohol is transmitted throughout the body via the blood stream and is progressively cleared from the blood primarily via the liver. Once alcohol has been cleared from the blood stream, individuals often experience what is commonly known as an "alcohol hangover," e.g., often simply referred to as a "hangover." A hangover refers to an array of physical symptoms that affect a person shortly after ingesting alcohol, e.g., within hours of consumption. The symptoms of a hangover include, for example, one or more of thirst, fatigue and/or weakness, headache and/or muscle aches, dizziness/faintness, loss of appetite, poor and/or decreased sleep, nausea and/or stomach pain (e.g., which can include vomiting), and elevated heart rate. A hangover is considered to be one of the most widely experienced negative consequences of consuming ethanol.

The hangover effect of alcohol consumption can vary based on the individual (e.g., body mass, age, hydration level, etc.), amount of alcohol ingested, and other ingredients, foods, or liquids consumed before, during, or after alcohol consumption. Despite the variability of parameters that affect the degree to which the symptoms of a hangover are 'felt' by an individual, the hangover effect occurs in an individual even if he or she does not have significant visible hangover symptoms, as the body has undergone the negative physical effects of alcohol even if the user is not consciously aware of it.

The present technology addresses problems caused by alcohol consumption including significant visible symptoms of a hangover consciously felt by the alcohol consumer, and also physical effects of the alcohol on the body that may not be consciously experienced. Disclosed are compositions, devices, and methods to prevent and recover from detrimental effects of alcohol consumption.

Usually alcohol is consumed through "alcoholic beverages." Alcoholic beverages are drinks that contain the molecule ethanol. Ethanol is the primary psychoactive ingredient in alcoholic beverages, e.g., including wine, beer, and distilled spirits. In the United States, for example, according to the NIAAA approximately 86% of Americans 18 or older reported that they have consumed alcoholic beverages at some point in their lifetime, with over 50% reporting that they have drank in the past month. Owing to the popularity of alcoholic beverages, alcohol can be considered as one of the most popular drugs in the world. According to the US Beverage Alcohol Forum, for 2012, the U.S. market size of alcoholic beverages was $197.8 billion in retail sales dollars.

Because a hangover can result in physically detrimental symptoms such lethargy, headaches and nausea, or other, it often reduces a person's ability to work at their normal or desired state. For example, a study of college students found that 25% had experienced a hangover in the previous week, and 29% reported losing school time for hangover recovery (e.g., Wiese et al, Annals of Internal Medicine 132 (11): 897-902, June 2000). In the same article, it was observed that 15% of men and women who have consumed alcohol experience hangovers at least monthly and ten percent of British men reported hangover-related problems at work at least monthly. Hangovers of individuals that consume alcohol at times proximate to their work schedule can cause economic losses. For example, it was estimated that 9.23% (e.g., 11.6 million workers) of the U.S. labor force work with a hangover and that alcohol use accounted for 3.3 billion (U.S.$) in lost wages each year, as a result of work missed because of a hangover suffered by the employee (e.g., Ling et al., Current drug abuse reviews 3 (2): 80-7, 2010). Similar results were shown for other countries such as Canada and Finland. Moreover, even if one does go to work with noticeable hangover symptoms, it has been noted that hangover severity and neurocognitive performance are significantly correlated, with more intense hangovers indicating less fitness for duty (e.g., Howland et al, Journal of Addiction Research Therapy (01), January 2010).

In a study reviewing hangovers, the physiological factors contributing to a hangover were identified as (1) dehydration and electrolyte imbalances, (2) gastrointestinal disturbances, (3) low blood sugar, (4) disruption of sleep and other biological rhythms, (5) headaches, (6) effects of alcohol withdrawal (AW), e.g., including irritability, anxiety, etc., and (7) toxic effects of acetaldehyde and congeners (e.g., Swift and Davidson, Alcohol Health Res. World, 22: 54-60, 1998). It has been shown by Wiese et al. that supplementation with B-Vitamins can decrease the severity of a hangover, implying that another cause of a hangover can include (8) vitamin loss. The brain is very B-Vitamin dependent, and a lack of nutrition causes physiological problems.

Acetaldehyde ($CH_3CHO$, also referred to as ethanal) is an aldehyde that is found in nature and also produced by the partial oxidation of ethanol in the liver by an enzyme alcohol dehydrogenase (ADH). Acetaldehyde is considered to be a contributing constituent that causes hangovers from alcohol consumption.

The liver acts to clear alcohol and acetaldehyde from the body. Alcohol consumption (and particularly over consumption) leads to liver stress and L-Glutathione depletion, leaving the individual with a temporarily overtaxed liver that cannot properly clear the body of toxins for a period of time during and after drinking. This over-taxation of the liver can lead to a buildup of lactic acid which known to be related to feelings of lethargy, e.g., and is thereby also considered to be another physiological factor contributing to hangovers: (9) reduced or impaired liver function in regards to added stress of alcohol on regular liver function. The present technology is capable of targeting these nine exemplary hangover causes in a comprehensive way.

Despite the increasing number of anti-hangover technologies available, none of the existing 'hangover cures' provide the alcohol consumer with a composition and/or methodology that is capable to counter all or at least most of the known causes of a hangover, and thereby are ineffective to prevent a potential hangover or to extensively improve the ability to recover from a multi-faceted (e.g., multi-symptomatic) hangover. Although some existing hangover remedies may be considered to be partially effective, there is still a need for a comprehensive solution that addresses a greater number of contributing factors for a hangover, if not all of the causes for a hangover. Existing hangover cures provide noncomprehensive or incomplete solutions that fail to identify or affect the full spectrum of causes and fail to provide comprehensive anti-hangover agent. Accordingly, the negative consequences of alcohol consumption continue to impair alcohol consumers globally, e.g., which have been shown to effect health and economies. The disclosed technology provides various compositions, formulations, delivery systems (e.g., capsules, powders, liquids) and methods for comprehensively treating and/or preventing hangovers, which target the full spectrum of hangover causes and provide more effective relief to persons consuming alcohol that can reduce at least some of the negative effects of alcohol.

Exemplary Embodiments

Various exemplary embodiments of the disclosed technology are illustrated in the following description and examples. In one embodiment, for example, a hangover prevention and/or treatment composition of the present technology includes dihydromyricetin (DHM), and N-acetyl cysteine (NAC). DHM is a compound also referred to as ampelopsin ((2R,3R)-3,5,7-trihydroxy-2-(3,4,5-trihydroxyphenyl)-2,3-dihydrochromen-4-one), which, for example, can be found in vine tea extract. DHM is understood to increase the rate at which alcohol and acetaldehyde are removed by the liver, and to reduce at least some of the negative effects of alcohol on the brain. DHM binds to the same receptors in the nervous system as alcohol binds to, e.g., $GABA_A$ receptor. By binding to the same receptor, DHM creates traffic at that receptor and thereby reduces alcohol's effects when taken with alcohol in the system, which can contribute to reducing AW symptoms. In some implementations of the exemplary hangover prevention and/or treatment composition, for example, the DHM (e.g., or extract of the plant from which it comes from, ampelopsin) is provided by the composition to combat the disruption of sleep and other biological rhythms, headaches, and the effects of alcohol withdrawal, i.e., the fourth, fifth, and sixth physiological factors listed above contributing to hangovers. For example, the DHM can also be provided by the composition to promote liver functionality in breaking down toxic substances, i.e., the ninth physiological factor contributing to hangovers. NAC is a natural precursor to L-Glutathione, which is an enzyme in the liver that breaks down acetaldehyde. In some implementations, for example, the NAC (e.g., or any of its functional substitutes such as SAM-e or L-Glutathione, or other) is provided by the composition to combat the toxic effects of acetaldehyde and congeners, i.e., the seventh physiological factor listed above contributing to hangovers.

In some implementations of the composition, for example, the DHM can be included in an amount of at least 300 mg. In some implementations of the composition, for example, the amount of DHM can be in a range between 300 mg and 3600 mg. In some implementations of the composition, for example, the NAC can be included in an amount of at least 25 mg. In some implementations of the composition, for example, the amount of NAC can be in a range between 25 mg and 1200 mg. In some implementations of the exemplary hangover prevention and/or treatment composition, for example, the amount of the DHM can be between 70 wt. % to 80 wt. % (e.g., 75 wt. %) and the amount of the NAC can be between 20 wt. % to 30 wt. % (e.g., 25 wt. %).

The composition can be incorporated into any of a variety of delivery systems, e.g., such as a capsule. In an example of a capsule (e.g., gelatin capsule) containing a 400 mg dose of the exemplary composition, the capsule can contain 300 mg of the DHM and 100 mg of the NAC. In another example of a capsule containing a 800 mg dose of the exemplary composition, the capsule can contain 600 mg of the DHM and 200 mg of the NAC. For example, the gelatin capsule can contain non-active ingredients adding to the mass of the composition's delivery system while not affecting the functionality of the composition. In some examples, a single 00size gelatin capsule can include non-active ingredients including gelatin, microcrystalline, cellulose, magnesium stearate, and food coloring to make capsule colors. In some implementations of the exemplary hangover prevention and/or treatment composition, for example, two 00size gelatin capsules each containing 600 mg of the DHM and 200 mg of the NAC may constitute a single dose of the composition.

In some embodiments of the composition, for example, the composition can further include Prickly Pear Extract and/or an extract of its active ingredient(s) (e.g., Tex-OE(R) or any other of its functional substitutes such as antioxidant constituents including Goji Berries, Kudzu Flower, or artichoke and/or the extracts of their active ingredients). Tex-OE(R) is a constituent of the prickly pear cactus capable of protecting cells from acetaldehyde, lactic acid, and toxins. For example, the Prickly Pear Extract can be provided by the composition to combat oxidative stress (e.g., toxic effects of acetaldehyde and congeners) that can cause inflammation, i.e., the seventh physiological factor listed above contributing to hangovers. In some implementations of the composition, for example, the Prickly Pear Extract can be included in an amount of at least 50 mg. In some implementations of the composition, for example, the amount of Prickly Pear Extract can be in a range between 50 mg and 1500 mg. In some implementations of an exemplary composition including DHM, NAC, and Prickly Pear Extract, for example, the amount of the DHM can be between 60 wt. % to 70 wt. % (e.g., 66.67 wt. %), the amount of the NAC can be between 15 wt. % to 30 wt. % (e.g., 22.2 wt. %), and the amount of Prickly Pear Extract can be between 5 wt. % to 20 wt. % (e.g., 11.1 wt. %). In an example of a capsule containing a 450 mg dose of the exemplary composition, the capsule can contain 300 mg of the DHM, 100 mg of the NAC, and 50 mg of the Prickly Pear Extract.

In some embodiments of the composition, for example, the composition can further include Milk Thistle and/or an extract of its active ingredient(s) (e.g., Silymarin, or any other of its functional substitutes). In some examples, the composition includes silibinin (INN) as the active ingredient of the silymarin constituent of the Milk Thistle. For example, the Milk Thistle can be provided by the composition to promote liver functionality in breaking down toxic substances and to combat oxidative stress (e.g., toxic effects of acetaldehyde and congeners), i.e., the seventh and ninth physiological factors listed above contributing to hangovers. In some implementations of the composition, for example, the Milk Thistle (e.g., Silymarin) can be included in an amount of at least 100 mg. In some implementations of the composition, for example, the amount of Milk Thistle (e.g., Silymarin) can be in a range between 100 mg and 500 mg. In some implementations of an exemplary composition including DHM, NAC, and Milk Thistle, for example, the amount of the DHM can be between 60 wt. % to 70 wt. % (e.g., 63.1 wt. %), the amount of the NAC can be between 15 wt. % to 30 wt. % (e.g., 21.1 wt. %), and the amount of Milk Thistle can be between 5 wt. % to 20 wt. % (e.g., 15.8 wt. %). In an example of a capsule containing a 475 mg dose of the exemplary composition, the capsule can contain 300 mg of the DHM, 100 mg of the NAC, and 75 mg of the Milk Thistle. In other implementations of an exemplary composition including DHM, NAC, Prickly Pear Extract and Milk Thistle, for example, the amount of the DHM can be between 50 wt. % to 65 wt. % (e.g., 57.1 wt. %), the amount of the NAC can be between 15 wt. % to 25 wt. % (e.g., 19.1 wt. %), the amount of Prickly Pear Extract can be between 5 wt. % to 15 wt. % (e.g., 9.5 wt. %), and the amount of Milk Thistle can be between 10 wt. % to 20 wt. % (e.g., 14.3 wt. %). In an example of a capsule containing a 525 mg dose of the exemplary composition, the capsule can contain 300 mg of the DHM, 100 mg of the NAC, 50 mg of the Prickly Pear Extract, and 75 mg of the Milk Thistle.

In some embodiments of the composition, for example, the composition can further include Ginger Root (e.g., including gingerol [(S)-5-hydroxy-1-(4-hydroxy-3-methoxyphenyl)-3-decanone], and/or (6)-Shogaol [(E)-1-(4-Hydroxy-3-methoxyphenyl)dec-4-en-3-one], and/or another of ginger's various constituents (which may be basic in pH) to combat gastrointestinal disturbances, i.e., the second physiological factor listed above contributing to hangovers. In some implementations of the composition, for example, the Ginger Root Extract (e.g., 5% gingerol) can be included in an amount of at least 25 mg. In some implementations of the composition, for example, the amount of Ginger Root Extract can be in a range between 25 mg and 1500 mg.

In some embodiments of the composition, for example, the composition can further include Vitamin B complex (e.g., Vitamins B1, B2, B3, B5, B6, B7, B9, and B12, or combinations thereof) to replenish vitamins lost with drinking alcohol (e.g., vitamins consumed in the alcohol breakdown process in the liver) and to combat headaches associated with a hangover, i.e., the eighth and fifth physiological factor listed above contributing to hangovers. In some implementations of the composition, for example, the Vitamin B complex or blend can be included in an amount of at least 25 mg. In some implementations of the composition, for example, the amount of Vitamin B complex or blend can be in a range between 25 mg and 400 mg. In some implementations, for example, the composition can include additional vitamins, e.g., including Vitamin C and Vitamin E. In some implementations of the composition, for example, the Vitamin C can be included in an amount of at least 50 mg. In some implementations of the composition, for example, the amount of Vitamin C can be in a range between 50 mg and 1000 mg. In some implementations of the composition, for example, the Vitamin E can be included in an amount of at least 30 IU. In some implementations of the composition, for example, the amount of Vitamin E can be in a range between 30 IU and 120 IU. In some implementations of an exemplary hangover prevention and/or treatment composition including DHM, NAC, Prickly Pear Extract, Milk Thistle, and B Vitamins, for example, the amount of the constituents can be as follows: DHM can be between 35 wt. % to 55 wt. % (e.g., 46.1 wt. %), the amount of the NAC can be between 10 wt. % to 20 wt. % (e.g., 15.4 wt. %), the amount of Prickly Pear Extract can be between 1 wt. % to 15 wt. % (e.g., 7.7 wt. %), the amount of Milk Thistle can be between 5 wt. % to 20 wt. % (e.g., 15.4 wt. %), and the amount of Vitamins B can be between 5 wt. % to 20 wt. % (e.g., 15.4 wt. %). In an example of a capsule containing a 260 mg dose of the exemplary composition, the capsule can contain 120 mg of the DHM, 40 mg of the NAC, 20 mg of the Prickly Pear Extract, 40 mg of the Milk Thistle, and 40 mg of the complete B Vitamin complex.

In some embodiments of the composition, for example, the composition further includes electrolytes and salts in various forms to combat dehydration and electrolyte imbalances and headaches associated with a hangover, i.e., the first and fifth physiological factors listed above contributing to hangovers. For example, electrolytes can include a mixture of some or all of the following exemplary electrolytes in their various forms: sodium, potassium, chloride, calcium, magnesium, bicarbonate, phosphate, and sulfate. For example, the salts can include sodium chloride (NaCl), potassium chloride (KCl), or other salts. In some implementations of the composition, for example, the electrolytes complex or blend mixture can be included in an amount of at least 50 mg. In some implementations of the composition, for example, the amount of electrolytes complex or blend mixture can be in a range between 50 mg and 800 mg.

In some embodiments of the composition, for example, the composition can further include sugars or carbohydrates in their various forms (e.g., such as glucose, dextrose, fructose, etc.) for the purpose to combat low blood sugar and headaches associated with a hangover, the third and fifth of the known hangover causes.

In some implementations of an exemplary hangover prevention and/or treatment composition including DHM, NAC, Prickly Pear Extract, Milk Thistle, Ginger Root, Vitamins, and electrolytes and salts, for example, the amount of the constituents can be as follows: DHM can be between 35 wt. % to 55 wt. % (e.g., 43.2 wt. %), the amount of the NAC can be between 10 wt. % to 20 wt. % (e.g., 14.4 wt. %), the amount of Prickly Pear Extract can be between 5 wt. % to 15 wt. % (e.g., 7.2 wt. %), the amount of Milk Thistle can be between 5 wt. % to 15 wt. % (e.g., 10.8 wt. %), the amount of Ginger Root can be between 1 wt. % to 10 wt. % (e.g., 3.6 wt. %), the amount of Vitamins B can be between 1 wt. % to 15 wt. % (e.g., 7.1 wt. %), the amount of Vitamins C can be between 1 wt. % to 15 wt. % (e.g., 7.2 wt. %), the amount of Vitamins E can be between 0.1 wt. % to 10 wt. % (e.g., 2.9 wt. %), and the amount of electrolytes and salts (e.g., NaCl and KCl) can be between 1 wt. % to 20 wt. % (e.g., 3.6 wt. %). In an example of a capsule containing a 695 mg dose of the exemplary composition, the capsule can contain 300 mg of the DHM, 100 mg of the NAC, 50 mg of the Prickly Pear Extract, 75 mg of the Milk Thistle, 25 mg of the Ginger Root, 15 mg of the Vitamin B1, 3 mg of the Vitamin B2, 3 mg of the Vitamin B3, 3 mg of the Vitamin B5, 5 mg of the Vitamin B6, 3 mg of the Vitamin B7, 3 mg of the Vitamin B9, 15 mg of the Vitamin B12, 50 mg of the Vitamin C, 20 mg (e.g., 30 IU) of the Vitamin E, 15 mg of the NaCl, and 10 mg of the KCl.

It should be noted that the exemplary embodiments of the disclosed technology include various formulations made from any of the above-mentioned compositions.

For example, the disclosed compositions include formulations of ingredients capable of effectively and comprehensively treating multiple symptoms of hangovers and the negative effects of alcohol. In some implementations, for example, compositions of the present technology can be used to aid in sobering up a person if taken during drinking, or keeping them sober if taken before drinking. In some implementations, for example, compositions of the present technology can be used as a daily supplement by individuals (e.g., such as individuals who regularly consume alcohol), e.g., which can aid in the replenishing of electrolytes of the individual, and/or reverse negative effects on brain function (e.g., through the use of DHM).

In implementations, a composition of the disclosed technology can be used before, during, or after the use of alcohol. For example, an exemplary hangover prevention and/or treatment composition could also be taken before going to sleep on the day or night of drinking, and/or again after waking (e.g., the next morning). The disclosed compositions can be contained in the form of capsules, tablets, or extended release capsules or tablets. In some implementations, for example, a composition of the disclosed technology can be contained in a liquid delivery mechanism, e.g., such that the exemplary composition was produced in the form of a drink (e.g., soft drink). In some implementations, for example, a composition of the disclosed technology can be made in the form of a liquid concentrate or shot which could be taken alone or added to water or a drink. In some implementations, for example, a composition of the disclosed technology can be made in the form of powder in a packet, e.g., in which the contents may be dispersed into water or a drink. The disclosed compositions can be used for sobering up, recovery from single or multiple exhibited hangover symptoms suffered after drinking, aiding in hangover prevention, in any of the above delivery forms (e.g., a pill, drink, liquid concentrate, packet of powder, or other solid form). In some implementations, for example, the disclosed compositions can be used as a daily supplement to aid in general health, e.g., particularly for individuals who regularly consume alcohol.

For example, administering the disclosed compositions in certain amounts and/or concentrations can treat or alleviate the symptoms of a hangover after the onset of the hangover has occurred. Also, for example, administering the disclosed compositions in certain amounts and/or concentrations can prevent the onset of a hangover. In some implementations, for example, the disclosed compositions may also increase sobriety when the composition is consumed before, during, or after immediately after alcohol consumption. In implementations, for example, the exemplary embodiments of the disclosed compositions can be administered in the form of example forms mentioned above (e.g., pills, drinks, liquid concentrates, and/or packets of powder).

Additional example embodiments of the disclosed hangover prevention and/or treatment composition are described.

In another example, a hangover prevention and/or treatment composition includes the electrolytes (e.g., one or a mixture of some or all of the following exemplary electrolytes in their various forms: sodium, potassium, chloride, calcium, magnesium, bicarbonate, phosphate, and sulfate); DHM; NAC; and Prickly Pear Extract.

In another example, a hangover prevention and/or treatment composition includes the electrolytes (e.g., one or a mixture of some or all of the following exemplary electrolytes in their various forms: sodium, potassium, chloride, calcium, magnesium, bicarbonate, phosphate, and sulfate); DHM; NAC; Prickly Pear Extract; and Ginger Root (e.g., or other constituent to lower stomach pH levels).

In another example, a hangover prevention and/or treatment composition includes the electrolytes (e.g., one or a mixture of some or all of the following exemplary electrolytes in their various forms: sodium, potassium, chloride, calcium, magnesium, bicarbonate, phosphate, and sulfate); DHM; NAC; Prickly Pear Extract; Ginger Root (e.g., or other constituent to lower stomach pH levels); and sugar or carbohydrates in their various forms (e.g., such as one or a mixture of some or all of the following exemplary carbohydrates: fructose, dextrose, and maltodextrin).

In another example, a hangover prevention and/or treatment composition includes the electrolytes (e.g., one or a mixture of some or all of the following exemplary electrolytes in their various forms: sodium, potassium, chloride, calcium, magnesium, bicarbonate, phosphate, and sulfate); DHM; NAC; Prickly Pear Extract; Ginger Root (e.g., or other constituent to lower stomach pH levels); sugar or carbohydrates in their various forms (e.g., such as one or a mixture of some or all of the following exemplary carbohydrates: fructose, dextrose, and maltodextrin); and a mixture of Vitamins B, C, and E (in any of their forms).

In another example, a hangover prevention and/or treatment composition includes the electrolytes (e.g., one or a mixture of some or all of the following exemplary electrolytes in their various forms: sodium, potassium, chloride, calcium, magnesium, bicarbonate, phosphate, and sulfate); DHM; NAC; Prickly Pear Extract; Ginger Root (e.g., or other constituent to lower stomach pH levels); sugar or carbohydrates in their various forms (e.g., such as one or a mixture of some or all of the following exemplary carbohydrates: fructose, dextrose, and maltodextrin); a mixture of Vitamins B, C, and E (in any of their forms); and Milk Thistle or its extract of Silymarin.

In some embodiments of the above exemplary compositions, for example, the composition can be formulated without DHM to be taken before alcohol consumption so as to avoid undergoing the sobering effects provided by the DHM. Similarly, in some embodiments of the above exemplary compositions, for example, the composition can be include two subcompositions including a first subcomposition formulated without DHM to be taken before alcohol consumption, and a second subcomposition formulated with DHM to be taken after alcohol consumption to maximize on the hangover preventing and/or curing effects.

In some implementations of the multiple subcombinations, for example, the first subcomposition can include NAC (e.g., of 25 wt. % to 50 wt. % (e.g., 44.5 wt. %)), Prickly Pear Extract (e.g., of 15 wt. % to 35 wt. % (e.g., 22.2 wt. %)), and Milk Thistle (e.g., of 20 wt. % to 40 wt. % (e.g., 33.3 wt. %)). In an example of a capsule containing a 225 mg dose of the exemplary first sub composition, the capsule can contain 200 mg of the NAC, 100 mg of the Prickly Pear Extract, and 150 mg of the Milk Thistle. For example, the second sub composition can include DHM (e.g., of 50 wt. % to 65 wt. % (e.g., 57.1 wt. %)), NAC (e.g., of 15 wt. % to 25 wt. % (e.g., 19.1 wt. %)), Prickly Pear Extract (e.g., of 5 wt. % to 15 wt. % (e.g., 9.5 wt. %)), and Milk Thistle (e.g., of 10 wt. % to 20 wt. % (e.g., 14.3 wt. %)). In an example of a capsule containing a 525 mg dose of the exemplary second sub composition, the capsule can contain 300 mg of the DHM, 100 mg of the NAC, 50 mg of the Prickly Pear Extract, and 75 mg of the Milk Thistle.

FIG. 1 shows a diagram of an exemplary method 100 for mitigating adverse effects of alcohol consumption using an exemplary multi-staged composition of the disclosed technology. The method 100 includes a process 110 to provide a dose of a first-stage composition including NAC, Prickly Pear Extract, and Milk Thistle at a first time proximate to the beginning of alcohol consumption by a user (i.e., the alcohol consumer). For example, in some implementations of the process 110, the first time can include two hours or less prior to (e.g., including just before) the beginning of the alcohol consumption. In some implementations of the process 110, for example, the first time can include within one hour after the beginning of the alcohol consumption by the user. In some implementations, for example, the first-stage composition can include the exemplary first sub combination previously described. In some implementations of the process 110, for example, the first-stage composition can also include one or more of ginger root extract, vitamins B complex or blend, vitamin C, vitamin E, electrolytes, and/or carbohydrates including sugar. In some implementations of the process 110, for example, the first-stage composition may include the Prickly Pear Extract or the Milk Thistle. For example, the first-stage composition can be provided by supplying the constituents of the first-stage composition (e.g., the NAC, and Prickly Pear Extract and/or Milk Thistle) in a delivery system, e.g., including a capsule, tablet, powder, liquid concentrate, or liquid mixture (e.g., drink).

The method 100 can include a process 120 to provide a dose of a second-stage composition including DHM, NAC, Prickly Pear Extract, and Milk Thistle at a second time proximate to the end of the alcohol consumption by the user. For example, in some implementations of the process 120, the second time can include two hours or less after (e.g., including just after) the end of the alcohol consumption. In some implementations of the process 120, for example, the second time can include within one hour before the end of the alcohol consumption by the user. In some implementations, for example, the second-stage composition can include the exemplary second sub combination previously described. In some implementations of the process 120, for example, the second-stage composition can also include one or more of ginger root extract, vitamins B complex or blend, vitamin C, vitamin E, electrolytes, and/or carbohydrates including sugar. In some implementations of the process 120, for example, the second-stage composition may include the Prickly Pear Extract or the Milk Thistle. For example, the second-stage composition can be provided by supplying the constituents of the second-stage composition (e.g., the DHM, NAC, and Prickly Pear Extract and/or Milk Thistle) in a delivery system, e.g., including a capsule, tablet, powder, liquid concentrate, or liquid mixture (e.g., drink).

The method 100 can include a process 130 to provide a dose of the second-stage composition at a third time after the alcohol consumption by the user. For example, in some implementations of the process 130, the third time can include several hours after (e.g., including four to twelve hours) the end of the alcohol consumption. For example, the third time can include after the user has slept after the alcohol consumption. In some implementations of the process 130, for example, the second-stage composition provided in the process 130 can include a third-stage composition that is provided at the third time that may differ in the constituents and/or their amounts or relative amounts than the second-stage composition.

In some implementations of the method 100, for example, the first-stage and the second-stage compositions can be provided as two distinctly visible delivery vehicles and/or packages. For example, the first-stage composition and the second stage composition may be provided as differing colors (e.g., blue pill vs. red pill) in a blister pack or pill container.

In some implementations of the method 100, for example, the method 100 can include the process 110, the process 120, and the process 130; whereas in some implementations, for example, the method 100 can include the process 110 and the process 120; or whereas in some implementations, for example, the method 100 can include the process 110 and the process 130.

EXEMPLARY IMPLEMENTATIONS

Some of the exemplary embodiments of the disclosed technology were prepared and utilized in exemplary implementations as described below.

EXEMPLARY FORMULATION 1

An exemplary capsule formulation was prepared as follows. 195 g of DHM (e.g., 98.6% pure) was added to a small mixing vat. To that was added 65 g of NAC to form a mixture. The mixture was then stirred to consistency, where there were no visible clumps or changes in color. Gelatin capsules were produced to contain the exemplary composition. For example, 400 gelatin capsules were mounted in the filling tray of a 400 rack 00# capsule size manual capsule filler. The mixture was then added to the filling tray and filled the capsules to max capacity, using a tamping tool to make sure max capacity was reached. After reaching max capacity, the gelatin capsule lids were mounted and pressed onto the capsule bottoms containing the powders, thus making complete capsules. When weighed, for example, the average capsule (empty) weighed 109 mg+/−1 mg (STDEV). After filled, the capsules weighed on average 760 mg+/−14 mg.

Exemplary Formulation 2

An exemplary capsule formulation was prepared as follows. 120 g of DHM (e.g., 98.6% pure) was added to a small mixing vat. To that was added 40 g of Milk Thistle (e.g., 80% Silymarin). To that mixture was added 40 g of a Vitamin B-Complex. To that mixture was added 40 g of NAC. And finally to that mixture was added 20 g of Prickly Pear Extract (4:1). The mixture was then stirred to consistency, where there were no visible clumps or changes in color. Gelatin capsules were produced to contain the exemplary composition. For example, 400 gelatin capsules were mounted in the filling tray of a 400 rack 00# capsule size manual capsule filler. The mixture was then added to the filling tray and filled the capsules to max capacity, using a tamping tool to make sure max capacity was reached. After reaching max capacity, the gelatin capsule lids were mounted and pressed onto the capsule bottoms containing the powders, thus making complete capsules. When weighed, for example, the average capsule (empty) weighed 109 mg+/−1 mg (STDEV). After filled, the capsules weighed on average 760 mg+/−14 mg.

Exemplary Formulation 3

An exemplary 16 oz soft drink formulation was prepared as follows. To form a sugar solution, 16 oz of water was added 15 g Sucrose syrup, 30 g glucose-fructose syrup, and citric acid. This was stirred until one solution. To this solution was added 900 mg of DHM (e.g., 98% pure), 300 mg of NAC, 150 mg of Prickly Pear Extract, 250 mg of Milk Thistle (e.g., 80% Silymarin), 150 mg of Vitamin C, 30 IU of Vitamin E, 200 mg of Sodium Chloride, 150 mg of Potassium Chloride, 45 mg of Ginger Root, 45 mg of Vitamin B1, 9 mg of Vitamin B2, 9 mg of Vitamin B3, 9 mg of Vitamin B5, 15 mg of Vitamin B6, 9 mg of Vitamin B7, 9 mg of Vitamin B9, and 45 mg of Vitamin B12. This was stirred until one solution was formed.

Exemplary Formulation 4

An exemplary effervescent tablet was prepared as follows, e.g. in which this formulation is designed to be taken before, during, or after alcohol consumption. 1000 g of DHM (e.g., 98.6% pure) was added to a mixing vat. To that was added 500 g of NAC. To that was added 200 g of Prickly Pear Fruit Powder. To that was added 300 g of Milk Thistle Extract (e.g., 80% pure Silymarin). To that was added 100 g of an electrolyte complex including 40 g sodium chloride and 60 g potassium citrate. To that was added 80 g of Ginger Root Extract containing greater than 5% gingerols by weight. To that was added 75 g of a vitamin complex including B-vitamins, Vitamin C, and Vitamin E, all at values higher than the US recommended daily allowance. To this mixture was then added sodium bicarbonate and citric acid used to release carbon dioxide and create an effervescent fizz. The sum total of this mixture was then mixed thoroughly until there was visible and physical consistency. The mixture was then pressed to form 100 effervescent tablets.

Exemplary Formulation 5

An exemplary gelatin capsule was prepared as follows, e.g. in which this formulation was designed to be taken before, after, or during alcohol consumption. 160 g of DHM (e.g., 98.6% pure) was added to a small mixing vat. To that was added 50 g of Milk Thistle Extract (e.g., 80% Silymarin). To that mixture was added 50 g of Prickly Pear Extract (4:1). The mixture was then stirred to consistency, where there were no visible clumps or changes in color. Gelatin capsules were produced to contain the exemplary composition. 400 gelatin capsules were mounted in the filling tray of a 400 rack 00# capsule size manual capsule filler. The capsules were then filled to max capacity, using a tamping tool to make sure capacity was reached. After reaching max capacity, the gelatin capsule lids were mounted and pressed onto the capsule bottoms containing the powders, thus making complete capsules. When weighed, for example, the average capsule (empty) weighed 109 mg+/−1 mg (STDEV). After filled, the capsules weighed on average 770 mg+/−18 mg.

Exemplary Formulation 6

An exemplary gelatin capsule was prepared as follows, e.g. in which this formulation was designed to be taken before, after, or during alcohol consumption. 160 g of DHM (e.g., 98.6% pure) was added to a small mixing vat. To that was added 33 g of Milk Thistle Extract (e.g., 80% Silymarin). To that mixture was added 33 g of Prickly Pear Extract (4:1). To that mixture was added 33 g of NAC. The mixture was then stirred to consistency, where there were no visible clumps or changes in color. Gelatin capsules were produced to contain the exemplary composition. 400 gelatin capsules were mounted in the filling tray of a 400 rack 00# capsule size manual capsule filler. The capsules were then filled to max capacity, using a tamping tool to make sure capacity was reached. After reaching max capacity, the gelatin capsule lids were mounted and pressed onto the capsule bottoms containing the powders, thus making complete capsules. When weighed, the average capsule (empty) weighed 109 mg+/−1 mg (STDEV). After filled, the capsules weighed on average 772 mg+/−16 mg.

Exemplary Formulation 7

An exemplary gelatin capsule was prepared as follows, e.g. in which this formulation was designed to be taken before drinking (e.g., possibly in same night as the exemplary formulation 7 below). 60 g of Prickly Pear Extract (4:1) was added to a small mixing vat. To that was added 60 g of Milk Thistle Extract (e.g., 80% Silymarin). To that mixture was added 30 g of a blend of Vitamins B, C, and E. To that mixture was added 50 g of NAC. To that mixture was added 50 g of electrolytes. To that mixture was added 10 g of Ginger Root (e.g., containing >5% Gingerols). The mixture was then stirred to consistency, where there were no visible clumps or changes in color. Gelatin capsules were produced to contain the exemplary composition. 400 gelatin capsules were mounted in the filling tray of a 400 rack 00# capsule size manual capsule filler. The capsules were then filled to max capacity, using a tamping tool to make sure capacity was reached. After reaching max capacity, the gelatin capsule lids were mounted and pressed onto the capsule bottoms containing the powders, thus making complete capsules. When weighed, for example, the average capsule (empty) weighed 109 mg+/−1 mg (STDEV). After filled, the capsules weighed on average 758 mg+/−13 mg.

Exemplary Formulation 8

An exemplary gelatin capsule was prepared as follows, e.g. in which this formulation was designed to be taken after drinking (e.g., possibly in same night as the exemplary formulation 6 above). 160 g of DHM (e.g., 98.6% pure) was added to a small mixing vat. To that was added 20 g of Milk Thistle Extract (e.g., 80% Silymarin). To that mixture was added 30 g of a blend of Vitamins B, C, and E. To that mixture was added 30 g of a Vitamin B, C, and E Complex. To that mixture was added 30 g of electrolytes. To that mixture was added 20 g of Ginger Root (containing >5% Gingerols). The mixture was then stirred to consistency, where there were no visible clumps or changes in color. Gelatin capsules were produced to contain the exemplary composition. 400 gelatin capsules were mounted in the filling tray of a 400 rack 00# capsule size manual capsule filler. The capsules were then filled to max capacity, using a tamping tool to make sure capacity was reached. After reaching max capacity, the gelatin capsule lids were mounted and pressed onto the capsule bottoms containing the powders, thus making complete capsules. When weighed, for example, the average capsule (empty) weighed 109 mg+/−1 mg (STDEV). After filled, the capsules weighed on average 752 mg+/−14 mg.

Exemplary Studies

Results from exemplary studies using the exemplary formulations are described. In one example study, 27 participants (e.g., 19 males and 8 females) underwent monitored alcohol consumption events where the participants drank alcoholic beverages of their choosing to their desired amount. The participants administered one or more of three different formulations of the composition (e.g., exemplary formulations 1, 2, and 3) after drinking alcohol, e.g., within two hours of the end of the alcohol consumption, but before going to sleep. The participants were given the exemplary formulations randomly so as to get an even number of participants testing each formulation (e.g., 9 per formulation). The participants were also studied under the same alcohol consumption scenarios without the use of the composition, i.e., control group.

The participants were instructed to fill out a quantitative survey shortly after waking from their sleep after the alcohol consumption events. In the survey, the participants answered questions directed to: their demographic and physical attributes, their drinking session experience, their activities surrounding their drinking experience, and their self-evaluation about their symptoms of a hangover on various levels. Participants quantitatively assessed the level of their hangover symptoms they felt after drinking alcohol without the composition and with the exemplary formulation of the composition.

For example, participants were asked to provide their gender, age, and weight (e.g., demographic and physical attributes information). For example, participants were asked to provide typical amounts and types of standard drinks consumed, and amount of time spent drinking in general, and the amount, type, and time spent drinking during the alcohol consumption events. Also, for example, the participants were asked questions regarding what they did in the prior 48 hours to the monitored alcohol consumption events, as well as what they did during and after drinking. Because various activities and chemicals can increase/decrease the likelihood and severity of hangovers, such parameters were considered for the quantitative analyses of the exemplary studies. For example, questions asked about the amount of sleep in 48 hours prior to (and immediately after) the alcohol consumption events, the amount of alcohol consumed in 48 hours prior to the alcohol consumption events, the amount of caffeine and/or nicotine consumed prior to (and immediately after) the alcohol consumption events, the amount of physical activity prior to (and during) the alcohol consumption events, and the level of nutrition received prior to, during, and after the alcohol consumption events. For example, the average age of the participants was 24, the average body weight was 167 lbs., the average number of alcoholic beverages consumed were 9 standard drinks, and the average time drinking during the monitored alcohol consumption events was 4.1 hrs.

Hangovers are the culmination of a large number of symptoms, such as: headaches, nausea and stomach pain, depression, anxiety, irritability, lethargy, brain fog, and mental and physical fatigue. Because of this, the participants were asked to rank the following symptoms on a scale of 1-10 for each symptom for the control (no composition taken) and for the experimental (composition taken) alcohol consumption events, e.g., in which 10 being the worst feeling, and 1 being feeling fine. For example, the symptoms are listed here with a numeric label for associated figures: headaches 201; stomach/ nausea 202; general energy/lethargy 203; focus/ ability to think clearly 204; mental energy/lethargy 205; physical energy/lethargy 206; general sense of well-being 207; motivation to perform daily activities 208; and general feeling about experiencing a hangover overall 209.

The data from the results from the exemplary studies were compiled and analyzed, and it was found that for each of the three exemplary compositions (e.g., the exemplary formulations 1, 2, or 3) that the participants experienced a greater than 50% positive change in their hangover symptoms by using the composition than by not using the composition. In other words, an average of 50%+ reduction in hangover symptoms were experienced across all three formulations, with one standard deviation being less than 27%.

Figure 2A:
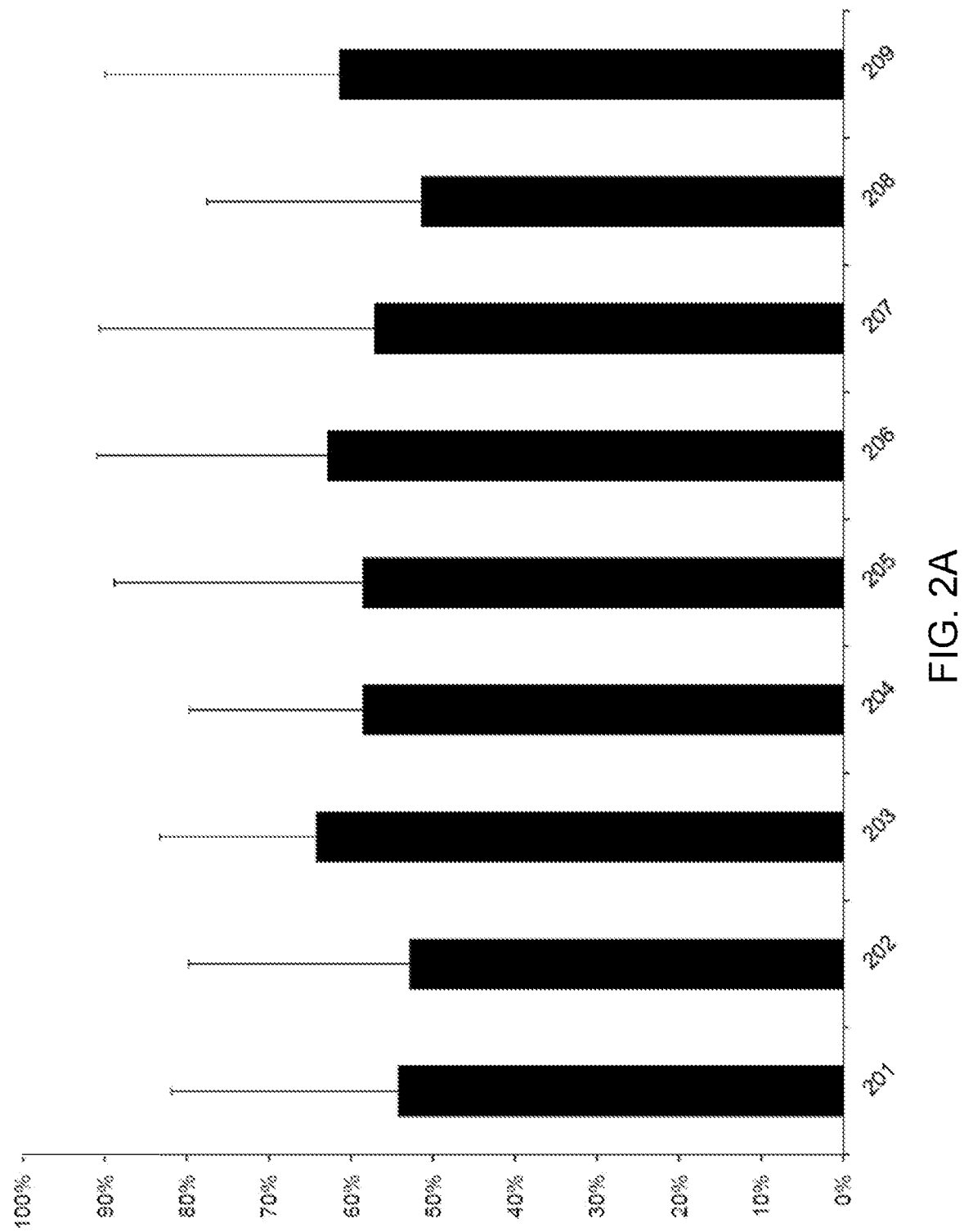
FIGS. 2A-2C show data plots of analyzed quantitative results obtained from the exemplary studies.
Figure 2B:
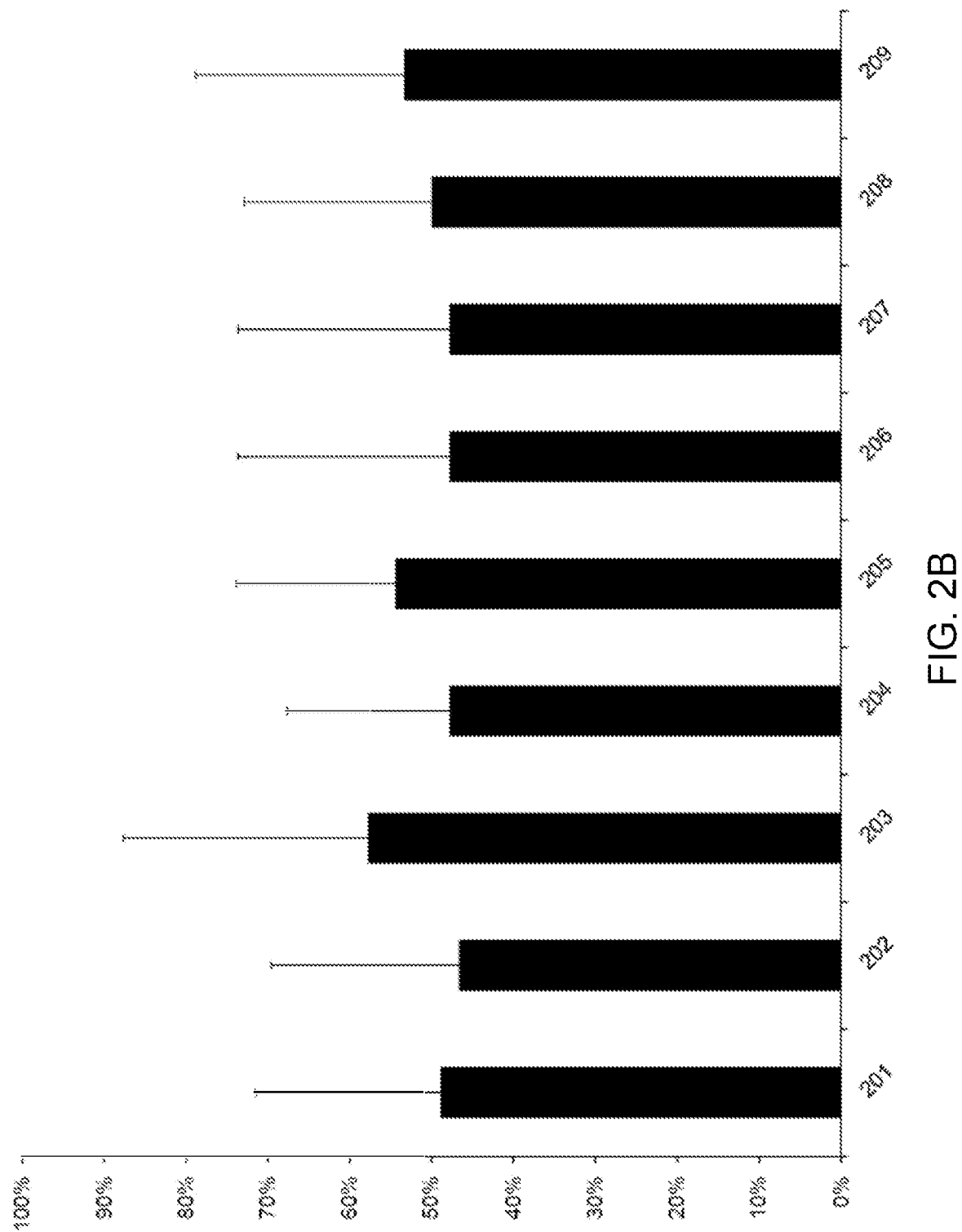
Figure 2C:
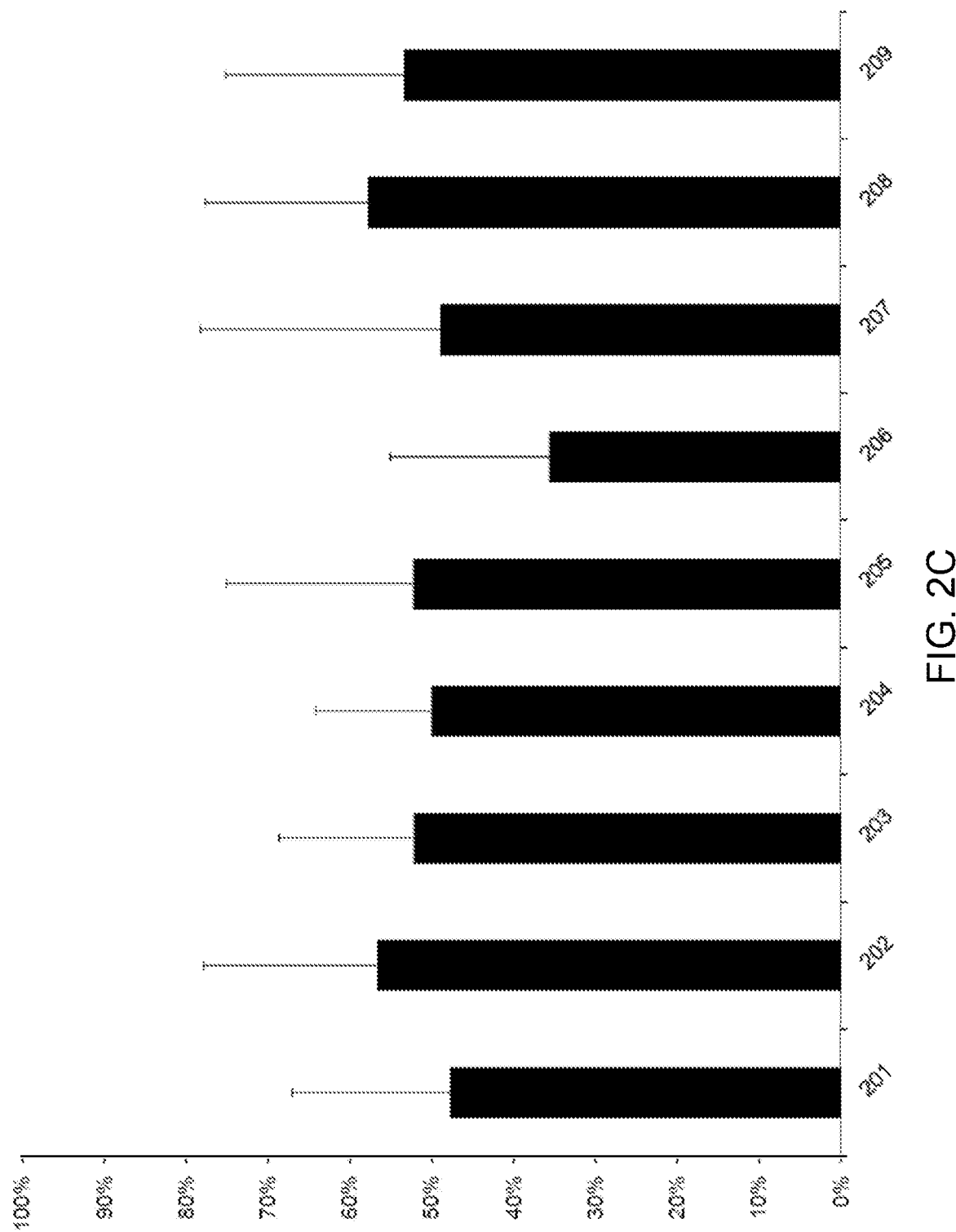

FIGS. 2A-2C show data plots of analyzed quantitative results obtained from the exemplary studies. FIG. 2A shows a data plot of the analyzed quantitative results using the exemplary formulation 1. FIG. 2B shows a data plot of the analyzed quantitative results using the exemplary formulation 2. FIG. 2C shows a data plot of the analyzed quantitative results using the exemplary formulation 3. In all of the data plots in FIGS. 2A-2C, the exemplary data showed that the average positive changes (between using the exemplary composition and not using the composition) were always at least a 50% reduction in hangover symptoms across the board. Moreover, the average median percent change (using the exemplary composition vs. not using the composition) were 61.1%, 56.7%, and 51.1% for the exemplary formulations 1, 2, and 3, respectively. Moreover, the standard deviation from the average mean percent change was always below 27% (as depicted by the error bars in the data plots of FIGS. 2A-2B) for all three exemplary compositions. There-fore, for example, for each of the exemplary formulations of the disclosed compositions, the composition was demonstrated to effectively reduce the symptoms of a hangover across the board.

EXAMPLES

The following examples are illustrative of several embodiments of the present technology. Other exemplary embodiments of the present technology may be presented prior to the following listed examples, or after the following listed examples.

In an example of the present technology (example 1), a composition includes dihydromyricetin (DHM); and N-acetyl cysteine (NAC).

Example 2 includes the composition of example 1, in which the composition includes between 70 wt. % to 80 wt. % of the DHM, and between 20 wt. % to 30 wt. % of the NAC.

Example 3 includes the composition of example 1, in which the DHM includes an amount of at least 300 mg, and the NAC includes an amount of at least 100 mg.

Example 4 includes the composition of example 1, in which a ratio of the DHM to the NAC is at least 3:1.

Example 5 includes the composition of example 1, further including prickly pear extract.

Example 6 includes the composition of example 5, in which the composition includes between 60 wt. % to 70 wt. % of the DHM, between 15 wt. % to 30 wt. % of the NAC, and between 5 wt. % to 20 wt. % of the prickly pear extract.

Example 7 includes the composition of example 5, in which the DHM includes an amount of at least 300 mg, the NAC includes an amount of at least 100 mg, and the prickly pear extract includes an amount of at least 50 mg.

Example 8 includes the composition of example 5, further including silymarin.

Example 9 includes the composition of example 8, in which the composition includes between 50 wt. % to 65 wt. % of the DHM, between 15 wt. % to 25 wt. % of the NAC, between 5 wt. % to 15 wt. % of the prickly pear extract, and between 10 wt. % to 20 wt. % of the silymarin.

Example 10 includes the composition of example 8, in which the DHM includes an amount of at least 300 mg, the NAC includes an amount of at least 100 mg, the prickly pear extract includes an amount of at least 50 mg, and the silymarin includes an amount of at least 100 mg.

Example 11 includes the composition of example 1, further including silymarin.

Example 12 includes the composition of example 11, in which the composition includes between 60 wt. % to 70 wt. % of the DHM, between 15 wt. % to 30 wt. % of the NAC, and between 5 wt. % to 20 wt. % of the silymarin.

Example 13 includes the composition of example 11, in which the DHM includes an amount of at least 300 mg, the NAC includes an amount of at least 100 mg, the prickly pear extract includes an amount of at least 50 mg, and the silymarin includes an amount of at least 100 mg.

Example 14 includes the composition of example 8, further including one or more B vitamins selected from a group consisting of thiamine, riboflavin, niacin, pantothenic acid, pyridoxine, pyridoxal, biotin, folic acid, and cobalamin.

Example 15 includes the composition of example 14, in which the composition includes between 35 wt. % to 55 wt. % of the DHM, between 10 wt. % to 20 wt. % of the NAC, between 1 wt. % to 15 wt. % of the prickly pear extract, between 5 wt. % to 20 wt. % of the silymarin, and 5 wt. % to 20 wt. % of the one or more B vitamins.

Example 16 includes the composition of example 14, in which the DHM includes an amount of at least 300 mg, the NAC includes an amount of at least 100 mg, the prickly pear extract includes an amount of at least 50 mg, the silymarin includes an amount of at least 100 mg, and the one or more B vitamins include an amount of at least 25 mg.

Example 17 includes the composition of examples 1, 5, 8, or 11, further including one or more of ginger root extract, vitamin C, vitamin E, electrolytes, or one or more B vitamins, in which the one or more B vitamins are selected from a group consisting of thiamine, riboflavin, niacin, pantothenic acid, pyridoxine, pyridoxal, biotin, folic acid, and cobalamin.

Example 18 includes the composition of example 17, in which the electrolytes include sodium chloride and potassium chloride.

Example 19 includes the composition of example 17, further including one or more carbohydrates including a sugar.

Example 20 includes the composition of example 17, in which the composition includes between 35 wt. % to 55 wt. % of the DHM, between 10 wt. % to 20 wt. % of the NAC, between 5 wt. % to 15 wt. % of the prickly pear extract, between 5 wt. % to 15 wt. % of the silymarin, between 1 wt. % to 10 wt. % of the ginger root extract, between 1 wt. % to 15 wt. % of the one or more B vitamins, between 1 wt. % to 15 wt. % of the vitamin C, between 0.1 wt. % to 10 wt. % of the vitamin E, and between 1 wt. % to 20 wt. % of the electrolytes.

Example 21 includes the composition of example 1, in which the composition is contained in a capsule, a tablet, a liquid concentrate, or a powder.

Example 22 includes the composition of example 1, further including Tex-OE(R).

Example 23 includes the composition of example 22, further including silibinin.

Example 24 includes the composition of example 1, further including silibinin.

Example 25 includes the composition of examples 1, 22, 23, or 24, further including one or more B vitamins selected from a group consisting of thiamine, riboflavin, niacin, pantothenic acid, pyridoxine, pyridoxal, biotin, folic acid, and cobalamin.

Example 26 includes the composition of example 25, further including one or more of (S)-5-hydroxy-1-(4-hydroxy-3-methoxyphenyl)-3-decanone, vitamin C, vitamin E, or electrolytes.

Example 27 includes the composition of example 26, further including one or more carbohydrates including a sugar.

Example 28 includes the composition of example 1, in which the composition is contained in a capsule, a tablet, a liquid concentrate, or a powder.

In an example of the present technology (example 29), a composition for mitigating adverse effects of alcohol consumption includes dihydromyricetin (DHM) of between 70 wt. % to 80 wt. % of the composition, in which the DHM is provided to reduce hangover symptoms including one or more of sleep disruption, headache, or alcohol withdrawal effects associated alcohol consumption; and N-acetyl cysteine (NAC) of between 20 wt. % to 30 wt. % of the composition, in which the NAC is provided to affect acetaldehyde and congeners produced by the liver associated with the alcohol consumption.

Example 30 includes the composition of example 29, further including prickly pear extract provided to affect oxidative stress associated with the alcohol consumption.

Example 31 includes the composition of example 30, in which the composition includes between 60 wt. % to 70 wt. % of the DHM, between 15 wt. % to 30 wt. % of the NAC, and between 5 wt. % to 20 wt. % of the prickly pear extract.

Example 32 includes the composition of examples 29 or 30, further including silymarin provided to affect liver functionality in breaking down toxic substances and to affect oxidative stress associated the alcohol consumption.

Example 33 includes the composition of example 32, in which the composition includes between 60 wt. % to 70 wt. % of the DHM, between 15 wt. % to 30 wt. % of the NAC, and between 5 wt. % to 20 wt. % of the silymarin.

Example 34 includes the composition of example 32, in which the composition includes between 50 wt. % to 65 wt. % of the DHM, between 15 wt. % to 25 wt. % of the NAC, between 5 wt. % to 15 wt. % of the prickly pear extract, and between 10 wt. % to 20 wt. % of the silymarin.

Example 35 includes the composition of examples 29 or 30, further including one or more B vitamins selected from a group consisting of thiamine, riboflavin, niacin, pantothenic acid, pyridoxine, pyridoxal, biotin, folic acid, and cobalamin, in which the one or more B vitamins are provided to replenish vitamins lost and to reduce headaches associated the alcohol consumption.

Example 36 includes the composition of example 29, further including prickly pear extract provided to affect oxidative stress associated with the alcohol consumption; silymarin provided to affect liver functionality in breaking down toxic substances and to affect oxidative stress associated the alcohol consumption; and one or more B vitamins selected from a group consisting of thiamine, riboflavin, niacin, pantothenic acid, pyridoxine, pyridoxal, biotin, folic acid, and cobalamin, in which the one or more B vitamins are provided to replenish vitamins lost and to reduce headaches associated the alcohol consumption.

Example 37 includes the composition of example 36, in which the composition includes between 35 wt. % to 55 wt. % of the DHM, between 10 wt. % to 20 wt. % of the NAC, between 1 wt. % to 15 wt. % of the prickly pear extract, between 5 wt. % to 20 wt. % of the silymarin, and 5 wt. % to 20 wt. % of the one or more B vitamins.

Example 38 includes the composition of examples 29, 30, or 36, further including one or more of: ginger root extract to reduce gastrointestinal hangover symptoms including one or both of nausea and vomiting, vitamin C and vitamin E to replenish vitamins lost and to reduce headaches associated the alcohol consumption, or electrolytes to affect dehydration and electrolyte imbalances and to reduce headaches associated the alcohol consumption.

Example 39 includes the composition of example 38, in which the composition includes between 35 wt. % to 55 wt. % of the DHM, between 10 wt. % to 20 wt. % of the NAC, between 5 wt. % to 15 wt. % of the prickly pear extract, between 5 wt. % to 15 wt. % of the silymarin, between 1 wt. % to 10 wt. % of the ginger root extract, between 1 wt. % to 15 wt. % of the one or more B vitamins, between 1 wt. % to 15 wt. % of the vitamin C, between 0.1 wt. % to 10 wt. % of the vitamin E, and between 1 wt. % to 20 wt. % of the electrolytes.

Example 40 includes the composition of example 38, further including one or more carbohydrates including a sugar.

Example 41 includes the composition of example 29, in which the composition is contained in a capsule, a tablet, a liquid concentrate, or a powder.

In an example of the present technology (example 42), a method for mitigating adverse effects of alcohol consumption includes providing a dose of a first-stage composition to be consumed at a first time proximate to the beginning of alcohol consumption by a person, in which the first-stage composition includes N-acetyl cysteine (NAC) and one or both of prickly pear extract and silymarin; and providing a dose of a second-stage composition to be consumed at a second time proximate to the end of the alcohol consumption by the person, or providing a dose of the second-stage composition or a third-stage composition to be consumed at a third time after the alcohol consumption by the user, in which the second-stage composition and the third-stage composition include dihydromyricetin (DHM), NAC, and one or both of one or both of prickly pear extract and silymarin.

Example 43 includes the method of example 42, in which the providing the dose of the first-stage composition includes supplying the NAC and the one or both of the prickly pear extract and the silymarin in a delivery system including a capsule, tablet, powder, liquid concentrate, or liquid mixture.

Example 44 includes the method of example 42, in which the providing the dose of the second-stage composition includes supplying the DHM, the NAC, and the one or both of the prickly pear extract and the silymarin in a delivery system including a capsule, tablet, powder, liquid concentrate, or liquid mixture.

In an example of the present technology (example MD, a method of mitigating the adverse effects of consuming alcohol includes identifying a person in need of hangover prophylaxis; and administering a formulation comprising ampelopsin and at least one compound chosen from N-acetyl cysteine, prickly pear extract, and silibinin to the said person in need of hangover prophylaxis.

Example M2 includes the method of example M1, including administering a formulation comprising ampelopsin, N-acetyl cysteine, prickly pear extract, and silibinin.

Example M3 includes the method of example M1, including administering the said formulation to a person having a blood alcohol concentration of greater than 0.08 grams per deciliter of blood.

Example M4 includes the method of example M3, including administering the said formulation to a person having a blood alcohol concentration of greater than 0.12 grams per deciliter of blood.

Example M5 includes the method of example M3, including administering the said formulation immediately prior to bedtime.

Example M6 includes the method of example M1, including administering a dry formulation.

Example M7 includes the method of example M6, including administering a tablet or capsule.

Example M8 includes the method of example M1, including administering one or more compounds chosen from thiamine, riboflavin, niacin, pantothenic acid, pyridoxine, pyridoxal, biotin, folic acid and cyanocobalamin.

In an example of the present technology (example C1), a synergistic anti-hangover formulation including electrolytes; vitamins; a liver support agent; an antioxidant; and a neurological support agent.

Example C2 includes the composition of example C1, in which the liver support agent is chosen from N-acetyl cysteine, Milk Thistle, and Silymarin.

Example C3 includes the composition of example C1, in which the neurological support agent is ampelopsin.

Example C4 includes the composition of example C1, in which the vitamins are chosen from B vitamins and vitamin C.

Example C5 includes the composition of example C1, including stomach discomfort relieving agent.

Example C6 includes the composition of example C5, including ginger root.

Example C7 includes the composition of example C5, including (E)-1-(4-Hydroxy-3-methoxyphenyl)dec-4-en-3-one.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A capsule or tablet consisting essentially of dihydromyricetin, L-cysteine, milk thistle extract, prickly pear extract, ginger root extract, at least one of sodium chloride or potassium citrate, and one or more B vitamins selected from the group consisting of thiamine, riboflavin, niacin, pantothenic acid, pyridoxine, pyridoxal, biotin, folic acid, and cyanocobalamin.

* * * * *